US009247872B2

(12) United States Patent
Iwase et al.

(10) Patent No.: US 9,247,872 B2
(45) Date of Patent: Feb. 2, 2016

(54) IMAGE PROCESSING APPARATUS AND IMAGE PROCESSING METHOD

(71) Applicant: Canon Kabushiki Kaisha, Tokyo (JP)

(72) Inventors: Yoshihiko Iwase, Kyoto (JP); Tomoyuki Makihira, Tokyo (JP); Makoto Sato, Tokyo (JP); Kazuhide Miyata, Yokohama (JP); Hiroyuki Shinbata, Tama (JP); Ritsuya Tomita, Kawasaki (JP); Daisuke Kibe, Chigasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/742,834

(22) Filed: Jan. 16, 2013

(65) Prior Publication Data

US 2013/0188135 A1    Jul. 25, 2013

(30) Foreign Application Priority Data

Jan. 20, 2012    (JP) ................................ 2012-010279
Aug. 27, 2012    (JP) ................................ 2012-186592

(51) Int. Cl.
*A61B 3/14* (2006.01)
*A61B 3/10* (2006.01)
*G01B 9/02* (2006.01)

(52) U.S. Cl.
CPC ............ *A61B 3/102* (2013.01); *G01B 9/02091* (2013.01)

(58) Field of Classification Search
CPC .............. A61B 3/00; A61B 3/10; A61B 3/14
USPC .................. 351/206, 205, 221, 210, 200, 246; 354/62
See application file for complete search history.

(56) References Cited

U.S. PATENT DOCUMENTS

| 5,719,399 | A | 2/1998 | Alfano et al. |
| 6,399,938 | B1 | 6/2002 | Sugawara et al. |
| 7,576,866 | B2 | 8/2009 | Ohkubo |
| 7,625,088 | B2 | 12/2009 | Fujita et al. |
| 7,648,242 | B2 | 1/2010 | Ferguson et al. |
| 7,973,939 | B2 | 7/2011 | Chou |

(Continued)

FOREIGN PATENT DOCUMENTS

| CN | 1917806 A1 | 2/2007 |
| CN | 101433458 A | 5/2009 |

(Continued)

OTHER PUBLICATIONS

Mircea Mujat et al., Autocalibration of spectral-domain optical coherence tomography spectrometers for in vivo quantitative retinal nerve fiber layer birefringence determination, Journal of Biomedical Optics, vol. 12, issue 4, article 041205, Jul. 30, 2007, Society of Photo-Optical Instrumentation Engineers, Bellingham WA, 2007.

(Continued)

*Primary Examiner* — Dawayne A Pinkney
(74) *Attorney, Agent, or Firm* — Canon USA, Inc., IP Division

(57) ABSTRACT

An image processing apparatus includes a tomographic image acquisition unit configured to acquire a polarization-sensitive tomographic image of a subject, and an extraction unit configured to extract, from the polarization-sensitive tomographic image of the subject, a region in which a polarization state is scrambled.

43 Claims, 8 Drawing Sheets

(56) References Cited

U.S. PATENT DOCUMENTS

| | | | |
|---|---|---|---|
| 8,334,982 B2 | 12/2012 | Fang-Yen et al. | |
| 8,376,547 B2 | 2/2013 | Hirose | |
| 8,427,654 B2 | 4/2013 | Horn et al. | |
| 8,463,016 B2 | 6/2013 | Pang | |
| 8,602,556 B2 | 12/2013 | Imamura | |
| 8,622,547 B2 | 1/2014 | Hayashi | |
| 8,764,737 B2 | 7/2014 | Kurtz et al. | |
| 2002/0091323 A1 | 7/2002 | Dreher | |
| 2007/0038040 A1 | 2/2007 | Cense et al. | |
| 2007/0070295 A1 | 3/2007 | Tsukada et al. | |
| 2007/0109554 A1 | 5/2007 | Feldchtein et al. | |
| 2007/0115481 A1 | 5/2007 | Toth et al. | |
| 2007/0211255 A1 | 9/2007 | Ohkubo | |
| 2007/0237445 A1 | 10/2007 | Hatori | |
| 2008/0100612 A1* | 5/2008 | Dastmalchi et al. | 345/418 |
| 2008/0151187 A1 | 6/2008 | Tsukada et al. | |
| 2008/0285043 A1 | 11/2008 | Fercher | |
| 2009/0115964 A1 | 5/2009 | Ueno | |
| 2009/0247862 A1* | 10/2009 | Meyer et al. | 600/425 |
| 2009/0310083 A1 | 12/2009 | Campbell et al. | |
| 2010/0166293 A1 | 7/2010 | Sugita et al. | |
| 2011/0137157 A1* | 6/2011 | Imamura et al. | 600/425 |
| 2011/0228222 A1 | 9/2011 | Kobayashi | |
| 2011/0267340 A1* | 11/2011 | Kraus et al. | 345/419 |
| 2011/0299034 A1 | 12/2011 | Walsh et al. | |
| 2012/0026464 A1 | 2/2012 | Berger et al. | |
| 2012/0140170 A1 | 6/2012 | Hirose et al. | |
| 2012/0249956 A1 | 10/2012 | Narasimha-Iyer et al. | |
| 2013/0003077 A1 | 1/2013 | Suehira et al. | |
| 2013/0070202 A1 | 3/2013 | Yonezawa et al. | |
| 2013/0182259 A1 | 7/2013 | Brezinski et al. | |
| 2013/0258349 A1 | 10/2013 | Makihira et al. | |
| 2013/0301006 A1 | 11/2013 | Kim et al. | |

FOREIGN PATENT DOCUMENTS

| | | |
|---|---|---|
| CN | 101986185 A | 3/2011 |
| CN | 102264281 A | 11/2011 |
| EP | 2243420 A | 10/2010 |
| JP | 2007-071728 A | 3/2007 |
| JP | 2007-240228 A | 9/2007 |
| JP | 2008-29467 A | 2/2008 |
| JP | 2008-508068 A | 3/2008 |
| JP | 2008-241585 A | 10/2008 |
| JP | 2008-264048 A | 11/2008 |
| JP | 2008-272256 A | 11/2008 |
| JP | 2009-507537 A | 2/2009 |
| JP | 2010-012111 A | 1/2010 |
| JP | 2010-029648 A | 2/2010 |
| JP | 2010-125291 A | 6/2010 |
| JP | 2011-19644 A | 2/2011 |
| JP | 2011-161007 A | 8/2011 |
| JP | 2011-212232 A1 | 10/2011 |
| JP | 2011-214969 A | 10/2011 |
| RU | 2344764 C1 | 1/2009 |
| WO | 2007/060973 A1 | 5/2007 |
| WO | 2007/103115 A2 | 9/2007 |
| WO | WO2008129864 A1 | 10/2008 |
| WO | 2008/139799 A1 | 11/2008 |
| WO | 2010/074279 A1 | 7/2010 |
| WO | 2010/101162 A1 | 9/2010 |
| WO | WO2010122118 A1 | 10/2010 |
| WO | 2012/004970 A1 | 1/2012 |

OTHER PUBLICATIONS

U.S. Appl. No. 13/742,666, filed Jan. 16, 2013, Yoshihiko Iwase.
U.S. Appl. No. 13/742,738, filed Jan. 16, 2013, Yoshihiko Iwase.
U.S. Appl. No. 13/743,083, filed Jan. 16, 2013, Yoshihiko Iwase.
U.S. Appl. No. 13/743,153, filed Jan. 16, 2013, Yoshihiko Iwase.
U.S. Appl. No. 13/743,216, filed Jan. 16, 2013, Yoshihiko Iwase.
U.S. Appl. No. 13/808,888, filed Jan. 7, 2013, Futoshi Hirose.
U.S. Appl. No. 13/808,895, filed Jan. 7, 2013, Futoshi Hirose.
Erich Gotzinger et al., Polarization Maintaining Fiber Based Ultra-High Resolution Spectral Domain Polarization Sensitive Optical Coherence Tomography, Optics Express, Nov. 25, 2009, 17(25):22704-22717, Optical Society of America, Washington, D.C., 2009.
Erich Götzinger et al., High Speed Spectral Domain Polarization Sensitive Optical Coherence Tomography of the Human Retina, Optics Express 13(25):10217-10229, Dec. 12, 2005, Optical Society of America, Washington, D.C.
D. A. Zimnyakov, V. V. Tuchin, Optical Tomography of Tissues, Quantum Electronics, 2002, 32(10):849-865, Kvantovaya Elektronika and Turpion Ltd, Moscow, RU, 2002.
Bernhard Baumann, Erich Götzinger, Michael Pircher, Christoph K. Hitzenberger, Single Camera Based Spectral Domain Polarization Sensitive Optical Coherence Tomography, Optics Express, Feb. 5, 2007, 15(3)1054-1063, OSA, Washington DC, 2007.
Erich Götzinger, Michael Pircher, Wolfgang Geitzenauer, Christian Ahlers, Bernhard Baumann, Stephan Michels, Ursula Schmidt-Erfurth, Christoph K. Hitzenberger, Retinal Pigment Epithelium Segmentation by Polarization Sensitive Optical Coherence Tomography, Optics Express, Oct. 15, 2008, 16(21):16410-16422, Optical Society of America, Washington DC, 2008.
E. Götzinger, M. Pircher, B. Baumann, C. Hirn, C. Vass, C, K. Hitzenberger, Retinal Nerve Fiber Layer Birefringence Evaluated With Polarization Sensitive Spectral Domain OCT and Scanning Laser Polarimetry: A Comparison, Journal of Biophotonics, Feb. 18, 2008, 1(2):129-139, WILEY-VCH Verlag GmbH & Co. KGaA, Weinheim, DE, 2008.

* cited by examiner

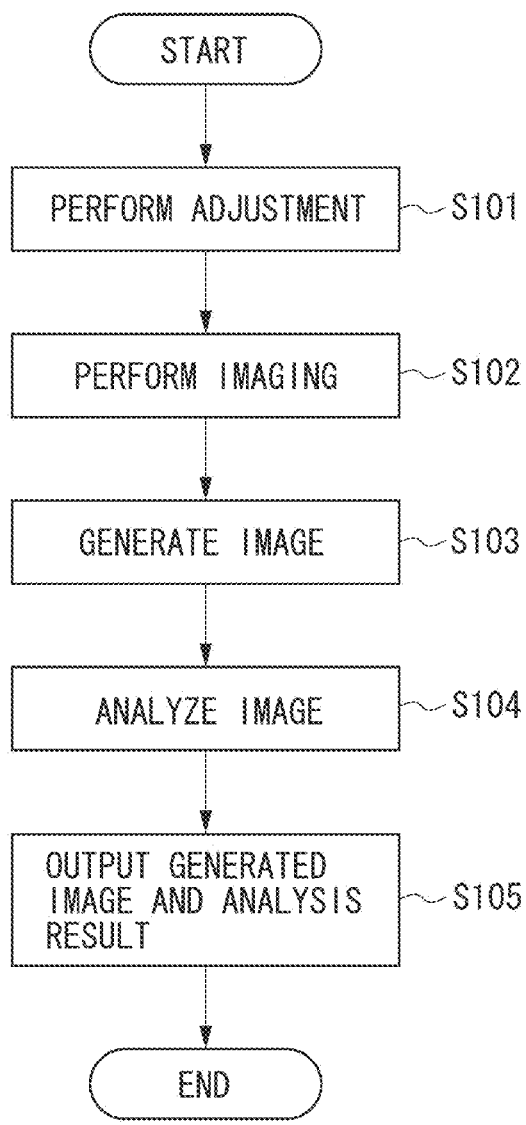

IMAGE PROCESSING APPARATUS AND IMAGE PROCESSING METHOD

BACKGROUND OF THE INVENTION

1. Field of the Invention

The present invention relates to an image processing apparatus and an image processing method for processing an image of a subject.

2. Description of the Related Art

An optical coherence tomography (OCT) technique using interference of multi-wavelength light enables acquisition of a high-resolution tomographic image of a sample (in particular, a fundus of the eye).

In recent years, an ophthalmologic OCT apparatus can acquire, in addition to a normal OCT image of a shape of a fundus tissue, a polarization-sensitive OCT image using a polarization parameter (i.e., retardation and orientation), which is an optical characteristic of the fundus tissue.

The polarization-sensitive OCT (PS-OCT) allows generation of the polarization-sensitive OCT image using the polarization parameter, and identification and segmentation of a fundus tissue. PS-OCT uses the fact that some layers in the retina (or fundus) of an eye reflect polarized light differently from other layers. International Publication No. WO 2010/122118 A1 discusses a polarization-sensitive OCT which employs, as a measuring beam for examining the sample, a light beam that has been modulated to a circularly-polarized beam. Detection is then performed by splitting the interference light into linearly-polarized beams perpendicular to each other, so that the polarization-sensitive OCT image is generated with different layers in the fundus being imaged differently depending on their interaction with the polarized light. However, International Publication No. WO 2010/122118 A1 does not discuss performing diagnosis support, i.e., the original objective of the polarization-sensitive OCT. More specifically, International Publication No. WO 2010/122118 A1 does not discuss a method for automatically detecting a retinal layer of the subject's eye from the polarization-sensitive OCT image. In general, there is a layer which can be more easily identified using the polarization-sensitive OCT image as compared to using the tomographic image acquired by employing a conventional OCT method.

SUMMARY OF THE INVENTION

The present invention is directed to an image processing apparatus capable of accurately extracting (detecting) a retinal layer of the subject's eye from the polarization-sensitive OCT image.

According to an aspect of the present invention, an image processing apparatus includes a tomographic image acquisition unit configured to acquire a polarization-sensitive tomographic image of a subject, and an extraction unit configured to extract, from the polarization-sensitive tomographic image of the subject, a region in which a polarization state is scrambled.

According to an exemplary embodiment of the present invention, the retinal layers of the subject's eye can be accurately extracted (detected) from the polarization-sensitive OCT image.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

FIG. 3 is a flowchart illustrating a process according to the present exemplary embodiment.

DESCRIPTION OF THE EMBODIMENTS

Various exemplary embodiments, features, and aspects of the invention will be described in detail below with reference to the drawings.

An imaging apparatus according to an exemplary embodiment of the present invention is applicable to a subject such as a subject's eye, skin, and an internal organ. Further, the imaging apparatus according to the present exemplary embodiment maybe an ophthalmologic apparatus or an endoscope.

Figure 1:
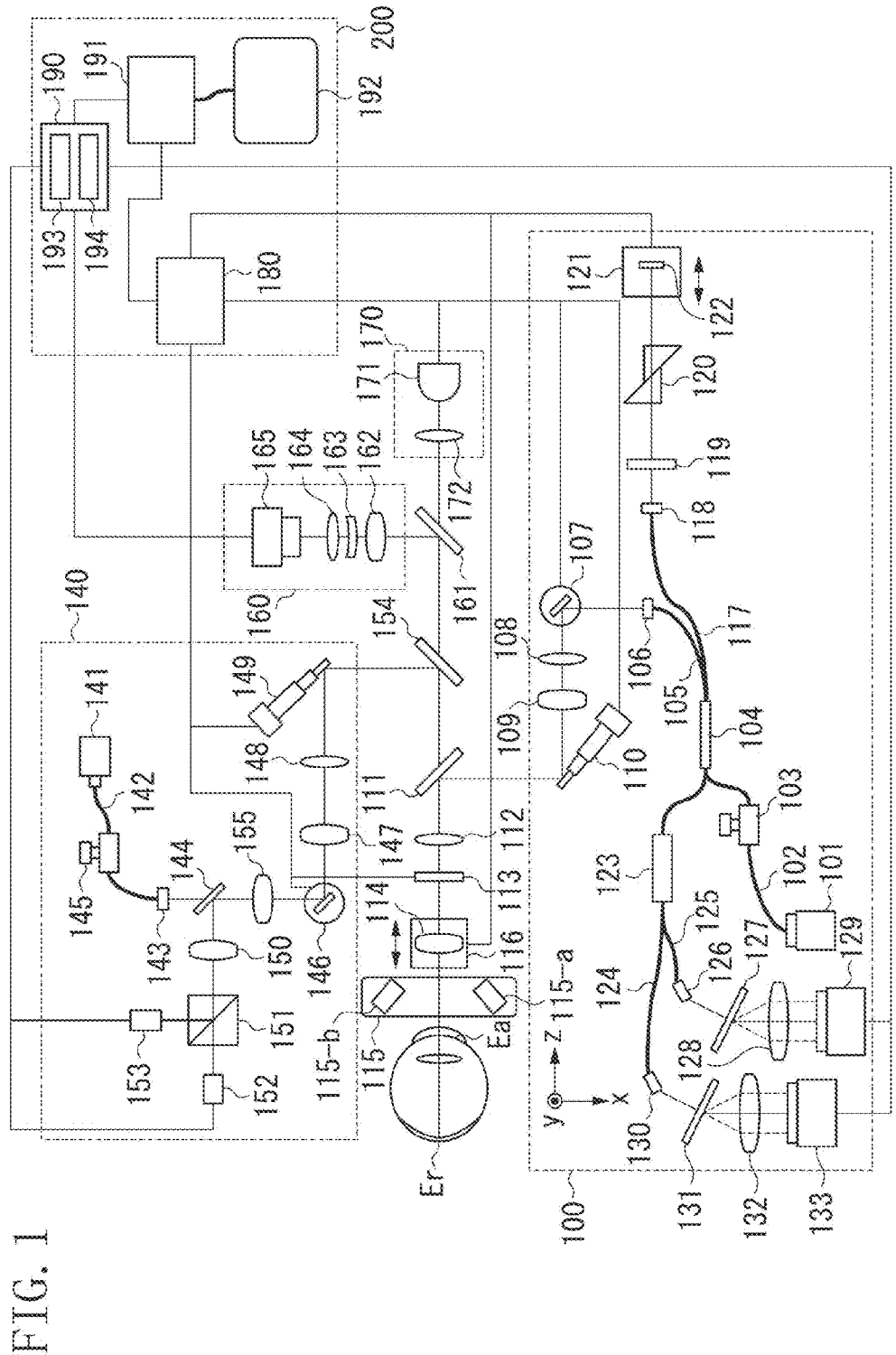
FIG. 1 is a schematic diagram illustrating an image processing apparatus according to an exemplary embodiment of the present invention.

FIG. 1 is a schematic diagram illustrating an ophthalmologic apparatus, which is an example of the imaging apparatus according to the present exemplary embodiment. At least a portion of a signal processing unit 190 to be described below may be considered as an image processing apparatus. In such a case, the ophthalmologic apparatus maybe considered as an ophthalmologic system, or the imaging system may be considered as an imaging system.

Referring to FIG. 1, the ophthalmologic apparatus includes a polarization-sensitive OCT (PS-OCT) 100, a polarization-sensitive scanning laser ophthalmoscope (PS-SLO) 140, an anterior segment imaging unit 160, an internal fixation lamp 170, and a control unit 200.

The ophthalmologic apparatus is aligned by lighting and causing the subject's eye to gaze at the internal fixation lamp 170, and using the image of the anterior segment of the subject captured by the anterior segment imaging unit 160. After completing the alignment, the PS-OCT 100 and the PS-SLO 140 perform imaging of the fundus.

The configuration of the PS-OCT 100 will be described below.

A light source 101 made of a super luminescent diode (SLD), i.e., a low-coherent light source, emits light having a central wavelength of 850 nm and a bandwidth of 50 nm. Any light source that can emit low coherent light, such as an amplified spontaneous emission (ASE) light source, maybe used as the light source 101.

The light emitted from the light source 101 is guided by a polarization maintaining (PM) fiber 102 and a polarization controller 103 to a fiber coupler 104 having a polarization preserving function. The beam is then split into a measuring beam (hereinafter referred to as a "measuring beam for a tomographic image", or an "OCT measuring beam") and a reference beam corresponding to the measuring beam.

The polarization controller 103 adjusts the polarization state of the beam emitted from the light source 101, and adjusts the beam to a linearly-polarized beam. A branching ratio of the fiber coupler 104 is 90 (reference beam):10 (measuring beam).

The measuring beam is output from a collimator 106 via a PM fiber 105 as a parallel beam. The output measuring beam reaches a dichroic mirror 111 via an X scanner 107, lenses 108 and 109, and a Y scanner 110. The X scanner 107 includes a galvano mirror that scans the measuring beam in a horizontal direction on a fundus Er, and the Y scanner 110 includes a galvano mirror that scans the measuring beam in a vertical direction on the fundus Er. The X scanner 107 and the Y scanner 110 are controlled by a drive control unit 180, and are capable of scanning the measuring beam in a desired range on the fundus Er. The range in which the measuring beam is scanned on the fundus may be considered as an acquisition range of the tomographic image, an acquisition position of the tomographic image, and an irradiation position of the measuring beam. Further, the X scanner 107 and the Y scanner 110 are examples of a scanning unit for PS-OCT, and may be configured as a common XY scanner. The dichroic mirror 111 reflects light having wavelengths of 800 nm to 900 nm, and transmits light of other wavelengths.

The measuring beam reflected off the dichroic mirror 111 passes through, via a lens 112, a $\lambda/4$ polarizing plate 113 arranged to be inclined at an angle of 45° from a P-polarization to an S-polarization with respect to an optical axis as a rotational axis. The phase of the beam is thus shifted by 90°, and is polarized to a circularly-polarized beam. The $\lambda/4$ polarizing plate 113 is an example of a polarization adjustment member for the measuring beam for adjusting the polarization state of the measuring beam. If a PS-SLO optical system to be described below is to be applied, the $\lambda/4$ polarizing plate 113 may be disposed in a common optical path between a portion of the PS-OCT optical system and a portion of the PS-SLO optical system. As a result, variation in the polarization states generated in the images acquired by the PS-OCT optical system and the PS-SLO optical system can be comparatively reduced. In such a case, the scanning unit for the PS-SLO and the scanning unit for the PS-OCT are arranged in mutually-conjugate positions, and may be arranged to be conjugate with a pupil in the subject's eye. The inclination of the $\lambda/4$ polarizing plate 113 is an example of a state of the $\lambda/4$ polarizing plate 113, and is an angle from a predetermined position in the case where the optical axis of a polarizing beam splitting surface of a fiber coupler 123 including a polarizing beam splitter is the rotating axis.

Further, the $\lambda/4$ polarizing plate 113 may be inserted and removed from the optical path. For example, the $\lambda/4$ polarizing plate 113 may be mechanically configured to rotate around the optical axis or an axis parallel to the optical axis as the rotational axis. As a result, a compact apparatus capable of easily switching between the SLO optical system and the PS-SLO optical system can be realized. Further, a compact apparatus capable of easily switching between the OCT optical system and the PS-OCT optical system can be realized.

The beam incident on the subject's eye is thus polarized to a circularly-polarized beam by arranging the $\lambda/4$ polarizing plate 113 to be inclined at an angle of 45°. However, the beam may not become a circularly-polarized beam on the fundus Er due to the characteristic of the subject's eye. To solve such a problem, the drive control unit 180 can perform control to finely adjust the inclination of the $\lambda/4$ polarizing plate 113.

A focus lens 114 mounted on a stage 116 focuses, on layers in a retina in the fundus Er via an anterior segment Ea of the subject's eye, the measuring beam polarized to a circularly-polarized beam. The measuring beam irradiating the fundus Er is reflected and scattered by each layer in the retina, and returns to the fiber coupler 104 via the above-described optical path.

On the other hand, the reference beam branched by the fiber coupler 104 is output as a parallel beam from a collimator 118 via a PM fiber 117. The output reference beam is polarized by a $\lambda/4$ polarizing plate 119 arranged to be inclined at an angle of 22.5° from the P-polarization to the S-polarization with the optical axis as the rotational axis, similarly as the measuring beam. The $\lambda/4$ polarizing plate 119 is an example of the polarization adjustment member for the reference beam for adjusting the polarization state of the reference beam. The reference beam is reflected via a dispersion compensation glass 120 by a mirror 122 mounted on a coherence gate stage 121, and returns to the fiber coupler 104. The reference beam passes through the $\lambda/4$ polarizing plate 119 twice, so that the linearly-polarized beam returns to the fiber coupler 104.

The coherence gate stage 121 is controlled by the drive control unit 180 to deal with differences in an axial length of the subject's eye. The coherence gate is the position corresponding to an optical path length of the reference beam in the optical path of the measuring beam. According to the present exemplary embodiment, the optical path length of the reference beam is changeable. However, it is not limited thereto, as long as the difference in the optical path lengths of the measuring beam and the reference beam can be changed.

The return beam and the reference beam that have returned to the fiber coupler 104 are combined into an interference beam (also referred to as a combined beam). The interference beam becomes incident on the fiber coupler 123 including the polarizing beam splitter, and is split at the branching ratio of 50:50 into a P-polarized beam and an S-polarized beam of different polarization directions.

The P-polarized beam is dispersed by a grating 131 via a PM fiber 124 and a collimator 130, and is received by a lens 132 and a line camera 133. The S-polarized beam is similarly dispersed by a grating 127 via a PM fiber 125 and a collimator 126, and is received by a lens 128 and a line camera 129. The gratings 127 and 131 and the line cameras 129 and 133 are arranged to match the direction of each polarization direction.

The beam received by each of the line cameras 129 and 133 is output as an electrical signal corresponding to the light intensity. The signal processing unit 190, which is an example of a tomographic image generation unit, then receives the output electrical signals.

The inclinations of the $\lambda/4$ polarizing plates 113 and 119 can be automatically adjusted based on the inclination of the polarizing beam splitter surface of the polarizing beam splitter. The inclinations of the $\lambda/4$ polarizing plates 113 and 119 can also be automatically adjusted with respect to a line connecting centers of an optic disk and a macula in the fundus. In such a case, it is desirable for an inclination detection unit (not illustrated) to detect the inclinations of the $\lambda/4$ polarizing plates 113 and 119. The inclination detection unit can detect the current inclination and detect whether the inclination has reached a predetermined inclination. Further, the inclinations of the $\lambda/4$ polarizing plates 113 and 119 can be detected based on the intensity of the received light, and the inclinations can be adjusted so that a predetermined intensity is reached. Furthermore, an object indicating the inclination may be displayed on a graphical user interface (GUI), and the user may adjust the inclination using a mouse. Moreover, a similar result can be acquired by adjusting a polarizing beam splitter and the λ/4 polarizing plates 113 and 119 based on the vertical direction as a polarization basis.

The configuration of the PS-SLO 140 will be described below.

According to the present exemplary embodiment, a light source 141, i.e., a semiconductor laser, emits a light beam having a central wavelength of 780 nm. The measuring beam emitted from the light source 141 (hereinafter referred to as a measuring beam for a fundus image, or an SLO measuring beam) is polarized via a PM fiber 142 by a polarizing controller 145 to a linearly-polarized beam, and is output from a collimator 143 as a parallel beam. The output measuring beam then passes through a perforated portion of a perforated mirror 144, and reaches, via a lens 155, a dichroic mirror 154 via an X scanner 146, lenses 147 and 148, and a Y scanner 149. The X scanner 146 includes a galvano mirror that scans the measuring beam in the horizontal direction on the fundus Er, and the Y scanner 149 includes a galvano mirror that scans the measuring beam in the vertical direction on the fundus Er. The X scanner 146 and the Y scanner 149 are controlled by the drive control unit 180, and are capable of scanning the measuring beam in the desired range on the fundus Er. Further, the X scanner 146 and the Y scanner 149 are examples of a scanning unit for the PS-SLO, and may be configured as a common XY scanner. The dichroic mirror 154 reflects light having wavelengths of 760 nm to 800 nm, and transmits light of other wavelengths.

The linearly-polarized measuring beam reflected by the dichroic mirror 154 reaches the fundus Er via the optical path similar to that of the PS-OCT 100.

The measuring beam irradiating the fundus Er is reflected and scattered by the fundus Er, and reaches the perforated mirror 144 via the above-described optical path. The beam reflected by the perforated mirror 144 is then split by a polarizing beam splitter 151 via the lens 150 into beams of different polarization directions (i.e., according to the present exemplary embodiment, split into a P-polarized beam and an S-polarized beam). The split beams are received by avalanche photodiodes (APD) 152 and 153, converted into electrical signals, and received by the signal processing unit 190, i.e., an example of the fundus image generation unit.

The position of the perforated mirror 144 is conjugate with the position of the pupil in the subject's eye. The perforated mirror 144 reflects the light that has passed through a peripheral region of the pupil among the light reflected and scattered by the fundus Er irradiated with the measuring beam.

According to the present exemplary embodiment, both the PS-OCT and the PS-SLO use the PM fiber. However, a similar configuration and effect maybe acquired by using a single mode fiber (SMF) in the case where the polarizing controller controls polarization.

The anterior segment imaging unit 160 will be described below.

The anterior segment imaging unit 160 irradiates the anterior segment Ea using an irradiation light source 115 including light emitting diodes (LED) 115-a and 115-b, which emit irradiation light having a wavelength of 1000 nm. The light reflected by the anterior segment Ea reaches a dichroic mirror 161 via the lens 114, the polarizing plate 113, the lens 112, and the dichroic mirrors 111 and 154. The dichroic mirror 161 reflects light having wavelengths of 980 nm to 1100 nm, and transmits light of other wavelengths. The light reflected by the dichroic mirror 161 is then received by an anterior segment camera 165 via lenses 162, 163, and 164. The light received by the anterior segment camera 165 is converted into an electrical signal and is received by the signal processing unit 190.

The internal fixation lamp 170 will be described below.

The interior fixation lamp 170 includes an interior fixation lamp display unit 171 and a lens 172. A plurality of LEDs arranged in a matrix shape is used as the interior fixation lamp display unit 171. A lighting position of the LED is changed by control performed by the drive control unit 180 according to a region to be imaged. The light emitted from the interior fixation lamp display unit 171 is guided to the subject's eye via the lens 172. The interior fixation lamp display unit 171 emits light having a wavelength of 520 nm, and the drive control unit 180 displays a desired pattern.

A control unit 200 for controlling the entire apparatus according to the present exemplary embodiment will be described below.

The control unit 200 includes the drive control unit 180, the signal processing unit 190, a display control unit 191, and a display unit 192.

The drive control unit 180 controls each unit as described above.

The signal processing unit 190 includes an image generation unit 193 and an image analysis unit 194. The signal processing unit 190 generates images, analyzes the generated images, and generates visualization information of the analysis results, based on the signals output from the line cameras 129 and 133, the APD 152 and 153, and the anterior segment camera 165. The processes for generating and analyzing the images will be described in detail below.

The display control unit 191 displays, on a display screen in the display unit 192, the images generated by a tomographic image generation unit and a fundus image generation unit and acquired by a fundus image acquisition unit (not illustrated) and a tomographic image acquisition unit (not illustrated). The display unit 192 may be a liquid crystal display. The image data generated by the signal processing unit 190 may be transmitted to the display control unit 191 via wired or wireless communication. In such a case, the display control unit 191 may be considered as the image processing apparatus. Further, the fundus image acquisition unit may include the SLO optical system, and the tomographic image acquisition unit may include the OCT optical system, as the imaging system. According to the present exemplary embodiment, if the subject is other than the subject's eye, the fundus image (i.e., a fundus intensity image) may be indicated as a planar image (i.e., a plane intensity image), and the fundus image acquisition unit as a planar image acquisition unit.

The display unit 192 displays display forms indicating various types of information to be described below based on control performed by the display control unit 191. Image data from the display control unit 191 may be transmitted to the display unit 192 via wired or wireless communication. Further, the display unit 192 is included in the control unit 200. However, it is not limited thereto, and the display unit 192 may be separated from the control unit 200. Furthermore, a tablet, which is an example of a portable device, configured by integrating the display control unit 191 and the display unit 192 may be used. In such a case, it is desirable to include a touch panel function in the display unit, so that a user can operate the touch panel to move the display position of the images, enlarge and reduce the images, and change the images to be displayed.

The image generation process performed by the image generation unit 193 included in the signal processing unit 190 will be described below.

The image generation unit 193 performs, on interference signals output from each of the line cameras 129 and 133, reconfiguration processing employed in a common spectral domain (SD-) OCT. The image generation unit 193 thus generates a tomographic image corresponding to a first polarized beam and a tomographic image corresponding to a second polarized beam, i.e., two tomographic images based on each polarization component.

More specifically, the image generation unit 193 performs fixed pattern noise cancellation on the interference signals. The fixed pattern noise cancellation is performed by averaging a plurality of A-scan signals that has been detected and thus extracting the fixed pattern noise, and subtracting the extracted fixed pattern noise from the input interference signal.

The image generation unit 193 then transforms the wavelength of the interference signal to a wave number, and performs Fourier transform, so that a tomographic signal indicating the polarization state is generated.

The image generation unit 193 performs the above-described process for the interference signals of the two polarization components, and thus generates the two tomographic images.

Further, the image generation unit 193 aligns the signals output from the APD 152 and 153 in synchronization with driving of the X scanner 146 and the Y scanner 149. The image generation unit 193 thus generates a fundus image corresponding to the first polarized beam and a fundus image corresponding to the second polarized beam, i.e., two fundus images based on each polarization component.

Furthermore, the image generation unit 193 generates a tomographic intensity image from the above-described two tomographic signals.

More specifically, the tomographic intensity image is basically the same as the tomographic image in the conventional OCT. A pixel value r of the tomographic intensity image is calculated from tomographic signals $A_H$ and $A_V$ acquired from each of the line cameras 129 and 133 using equation (1).

$$r = \sqrt{A_H^2 + A_V^2} \quad (1)$$

Moreover, the image generation unit 193 similarly generates a fundus intensity image from the two fundus images.

Figure 2A:
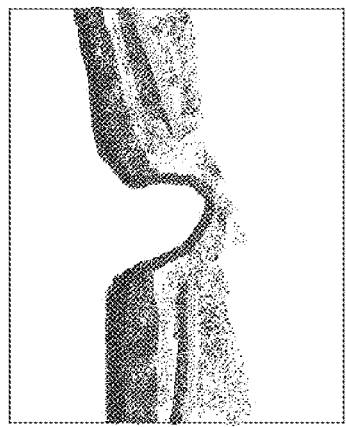
FIGS. 2A, 2B, 2C, 2D, and 2E illustrate examples of images generated by a signal processing unit.

FIG. 2A illustrates an example of the intensity image of the optic disk.

When the λ/4 polarizing plate 113 is removed from the optical path, the display control unit 191 may display, on the display unit 192, the tomographic intensity image acquired employing the conventional OCT technique, or the fundus intensity image acquired employing the conventional SLO technique.

Further, the image generation unit 193 generates a retardation image from the tomographic images of the polarization components that are perpendicular to each other.

A value δ of each pixel in the retardation image is a value indicating a ratio of the effects received by the vertical polarization component and the horizontal polarization component in the subject's eye, at the position of each pixel configuring the tomographic image. The value δ is calculated from each of the tomographic signals $A_H$ and $A_V$ using equation (2).

$$\delta = \arctan\left[\frac{A_V}{A_H}\right] \quad (2)$$

Figure 2B:
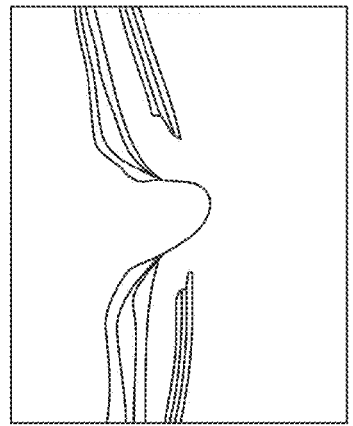

FIG. 2B illustrates an example of the retardation image of the optic disk generated as described above. The retardation image can be acquired by calculating equation (2) for each B-scan image. As described above, the retardation image is a tomographic image indicating the difference of the effect received by the two polarized beams in the subject's eye. Referring to FIG. 2B, the values indicating the above-described ratio are displayed as a color tomographic image. A darker-shaded portion indicates that the value of the ratio is small, and a lighter-shaded portion indicates that the value of the ratio is large. As a result, generating the retardation image enables recognizing a layer in which there is birefringence. For further details, refer to "Erich Götzinger et al., Optics Express 13(25):10217-10229, Dec. 12, 2005, Optical Society of America, Washington, D.C.".

Furthermore, the image generation unit 193 can similarly generate a retardation image in a planar direction of the fundus based on the outputs from the APD 152 and 153.

The image generation unit 193 generates a retardation map from the retardation images acquired with respect to a plurality of B-scan images.

More specifically, the image generation unit 193 detects a retinal pigment epithelium (RPE) in each B-scan image. Since the RPE cancels polarization, the image generation unit 193 searches for a retardation distribution of each A-scan along the depth direction in the range from an inner limiting membrane (ILM) without including the RPE. The image generation unit 193 then sets a maximum value of the retardation as a representative value of the retardation in the A-scan.

The image generation unit 193 performs the above-described process on all retardation images, and thus generates the retardation map.

Figure 2E:
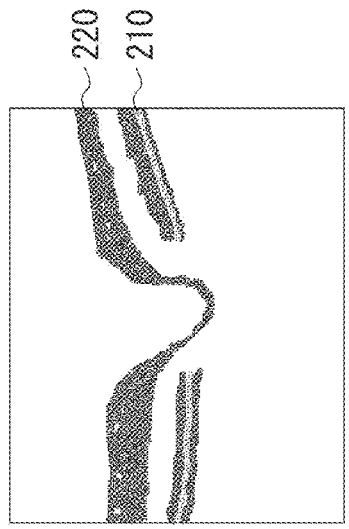
Figure 2D:
Figure 2C:
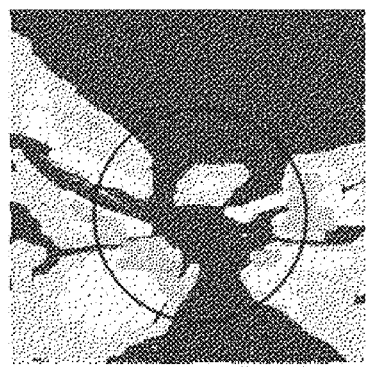

FIG. 2C illustrates an example of the retardation map of the optic disk. Referring to FIG. 2C, the darker-shaded portion indicates that the value of the ratio is small, and the lighter-shaded portion indicates that the value of the ratio is large. The layer having birefringence in the optic disk is a retinal nerve fiber layer (RNFL), and the retardation map illustrates the value indicating the ratio caused by the birefringence in the RNFL and the thickness of the RNFL. As a result, the value indicating the ratio becomes large where the RNFL is thick, and becomes small where the RNFL is thin. The thickness of the RNFL for the entire fundus thus becomes recognizable using the retardation map, and can be used in the diagnosis of glaucoma.

The image generation unit 193 performs linear approximation of the value of the retardation δ in the range of ILM to RNFL in each A scan image of the previously generated retardation image. The image generation unit 193 then determines the acquired slope as the birefringence at the position on the retina in the A-scan image. In other words, since retardation is a product of a distance and the birefringence in the RNFL, a linear relation is acquired by plotting the depth and the value of the retardation in each A-scan image. As a result, linear approximation is performed on the plot using a least square method, and the acquired slope becomes the value of the birefringence in the RNFL in the A-scan image. The image generation unit 193 performs the above-described process on all of the acquired retardation images, and generates the map representing the birefringence.

FIG. 2D illustrates an example of the birefringence map of the optic disk. The birefringence map directly maps the values of the birefringence. As a result, when a fibrous architecture of the RNFL changes even if the thickness of the RNFL does not change, the change can be visualized as the change in the birefringence.

The image generation unit 193 calculates a Stokes vector S for each pixel from the acquired tomographic signals $A_H$ and $A_V$, and a phase difference $\Delta\Phi$ between the tomographic signals $A_H$ and $A_V$, using equation (3).

$$S = \begin{pmatrix} I \\ Q \\ U \\ V \end{pmatrix} = \begin{pmatrix} A_H^2 + A_V^2 \\ A_H^2 - A_V^2 \\ 2A_H A_V \cos\Delta\phi \\ 2A_H A_V \sin\Delta\phi \end{pmatrix} \quad (3)$$

In such a case, $\Delta\Phi$ is calculated from phases $\Phi_H$ and $\Phi_V$ of each signal acquired when calculating the two tomographic images, as $\Delta\Phi=\Phi_V-\Phi_H$.

The image generation unit 193 then sets, in each B-scan image, a window of the size that is proximately 70 μm in a main scanning direction of the measuring beam and 18 μm in a depth direction. The image generation unit 193 then averages each element of the Stokes vector calculated for each pixel by a number C within each window, and calculates a degree of polarization uniformity (DOPU) within the window using equation (4).

$$\text{DOPU} = \sqrt{Q_m^2 + U_m^2 + V_m^2} \quad (4)$$

In equation (4), $Q_m$, $U_m$, and $V_m$ are values acquired by averaging the elements Q, U, and V in the Stokes vector within each window. The image generation unit 193 performs the above-described process for all windows in the B-scan images, and generates a DOPU image of the optic disk as illustrated in FIG. 2E. As described above, the DOPU image is a tomographic image indicating the degree of polarization uniformity of the two types of polarization.

DOPU is a value indicating the uniformity of polarization, and becomes close to "1" when polarization is preserved, and smaller than "1" when polarization is cancelled (scrambled) or not preserved. Since the RPE in the structure of the retina cancels the polarization state, the value of the DOPU in the portion corresponding to the RPE in the DOPU image becomes lower than the values in the other portions. Referring to FIG. 2E, the lighter-shaded portion indicates the RPE 210, and the darker-shaded portion indicates the retinal layer 220. The DOPU image visualizes the layer such as the RPE that cancels polarization, so that the image of the RPE can be firmly acquired as compared to the change in the intensity even when the RPE is deformed due to a disease.

Further, the image generation unit 193 can similarly generate a DOPU image in the planar direction of the fundus based on the outputs from the APD 152 and 153.

According to the present exemplary embodiment, the above-described tomographic images corresponding to the first and second polarized beams, the retardation image, and the DOPU image will be referred to as tomographic images indicating the polarization state. Further, according to the present exemplary embodiment, the above-described retardation map and the birefringence map will also be referred to as fundus images indicating the polarization state.

The operation performed in the image processing apparatus according to the present exemplary embodiment will be described below.

FIG. 3 is a flowchart illustrating the operation performed by the image processing apparatus according to the present exemplary embodiment.

In step S101, the image processing apparatus and the subject's eye positioned on the image processing apparatus are aligned. The process unique to the present exemplary embodiment with respect to performing alignment will be described below. Since alignment of a working distance in X, Y, and Z directions, focusing, and adjustment of the coherence gate are common, description will be omitted.

Figure 4:
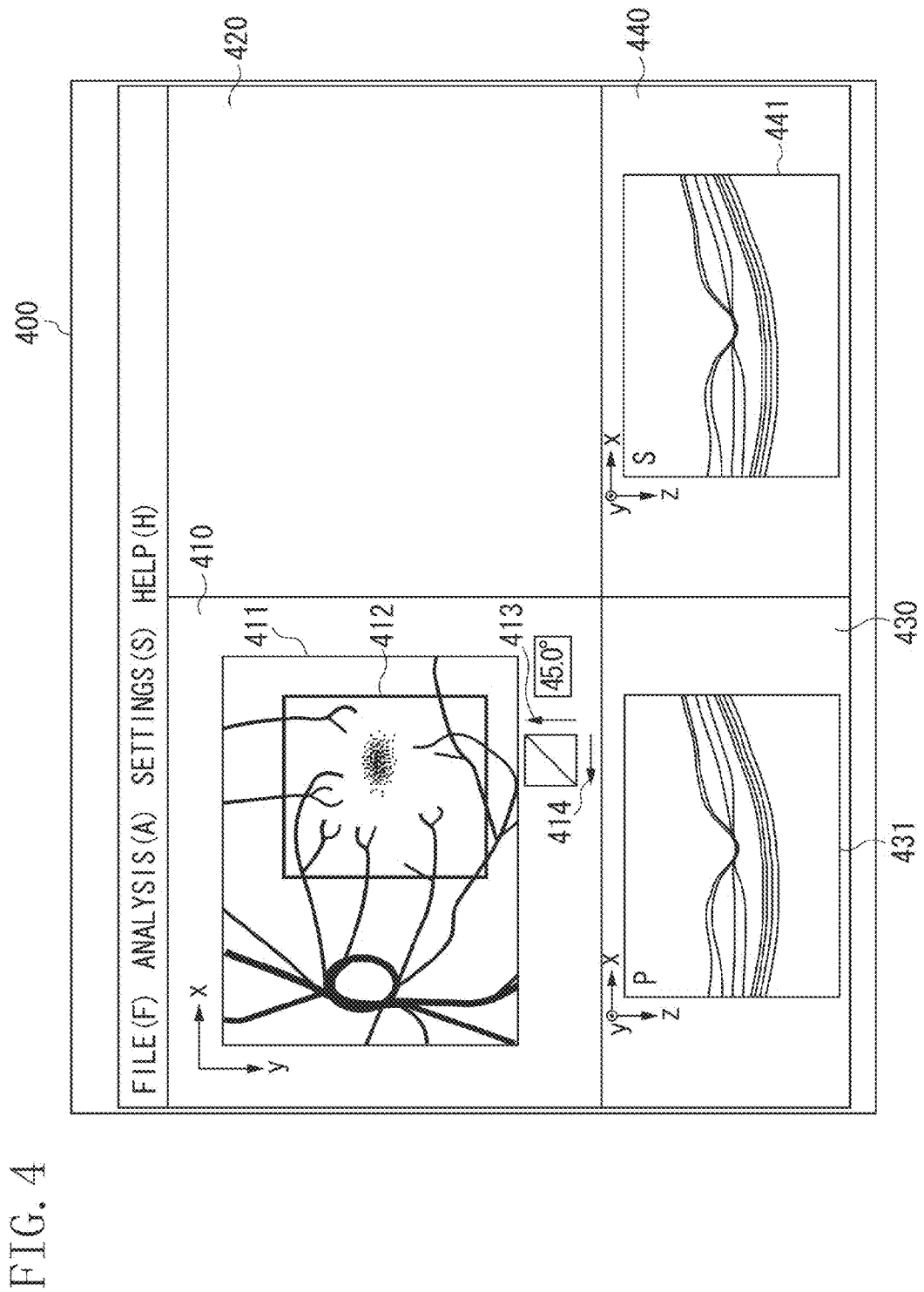
FIG. 4 illustrates a display example of a display screen on a display unit in the image processing apparatus according to the present exemplary embodiment.

FIG. 4 illustrates a window 400 displayed on the display unit 192 when performing adjustment. Referring to FIG. 4, a display area 410, i.e., an example of a first display area, displays a fundus image 411 imaged by the PS-SLO 140 and generated by the signal processing unit 190. A frame 412 indicating an imaging range of the PS-OCT 100 is superimposed on the fundus image 411.

An operator sets the imaging range under control of the drive control unit 180, by clicking and dragging an instruction device (not illustrated), such as a mouse, and designating by a cursor displayed on the window 400. In other words, the operator designates the frame 412 using the cursor, and moves the frame 412 by the dragging operation. As a result, the drive control unit 180 controls a drive angle of a scanner and sets the imaging range. According to the present exemplary embodiment, the mouse includes a sensor for detecting a movement signal when the user manually moves the mouse in two directions, left and right mouse buttons for detecting that the user has pressed the button, and a wheel mechanism between the two mouse buttons which is movable in front and back and left to right directions. Further, the display unit may include a touch panel function, and the operator may designate the acquisition position on the touch panel.

The adjustment of the λ/4 polarizing plate 113 will be described below.

Referring to FIG. 4, indicators 413 and 414 are displayed for adjusting the angle of the λ/4 polarizing plate 113. When the user instructs using the instruction device, the angle of the λ/4 polarizing plate 113 is adjusted based on control of the drive control unit 180. The indicator 413 is for instructing adjustment in a counterclockwise direction, and the indicator 414 is for instructing adjustment in a clockwise direction. A numerical value displayed besides the indicators 413 and 414 indicates the current angle of the λ/4 polarizing plate 113. The display control unit 191 may display the indicator for adjusting the angle of the λ/4 polarizing plate 119 side by side with the indicator 413 on the display unit 192, or in place of the indicator 413.

The operator gives, using the cursor by operating on the mouse, an instruction so that the intensities of the tomographic images of each polarized beam respectively displayed on a display area 430, i.e., an example of a third display area, and a display area 440, i.e., an example of a fourth display area, become the same. A peak intensity value may be displayed along with tomographic images 431 and 441 of each polarized beam, or a waveform of each interference signal may be displayed, so that the operator performs adjustment while viewing the peak intensity value or the waveform. The tomographic images 431 and 441 of each polarized beam are examples of tomographic images corresponding to the first polarized beam and the second polarized beam, respectively. It is desirable to display a type of each image on the tomographic images 431 and 441 of each polarized beam (or tomographic images 531 and 541 to be described below). For example, a letter "P" indicating the P-polarized beam and a letter "S" indicating the S-polarized beam may be displayed. As a result, such a display prevents the user from misrecognizing the image. The letters may be displayed above or besides the image instead of being superimposed on the image, as long as the display is arranged to be associated with the image.

It is not necessary at this point for a display area 420, i.e., an example of a second display area, to display any information. If auto adjustment is to be performed, the current adjustment state, such as a message informing "adjusting λ/4 polarizing plate", may be displayed on the display area 420. Further, a display indicating patient information such as a left eye or a right eye, or image capturing information such as an image capturing mode may be performed on the window 400. Furthermore, it is desirable to repeatedly insert and remove the λ/4 polarizing plate 113 with respect to the optical path for alternately acquiring the fundus intensity image and the tomographic image indicating the polarization state. As a result, the display control unit 191 even in a minimum-sized ophthalmologic apparatus can display the fundus intensity image on the display area 410 and the tomographic image indicating the polarization state on the display area 420.

It is desirable to perform adjustment in the following order: alignment adjustment using the anterior segment image or a luminescent spot in a cornea; focus adjustment using the fundus image indicating the polarization state; coherence gate adjustment using the tomographic image indicating the polarization state; and adjustment of the λ/4 polarizing plate. Further, it is desirable to determine the acquisition position of the tomographic image indicating the polarization state before adjusting the coherence gate using the tomographic image indicating the polarization state. However, the acquisition position maybe determined in an initial setting for acquiring a center region of the fundus image indicating the polarization state. Adjustment can thus be simply performed to accurately acquire the tomographic image indicating the polarization state that is finer and corresponding to a narrower range as compared to the fundus image indicating the polarization state. In such a case, the λ/4 polarizing plate may be automatically adjusted in response to completion of adjustment of the coherence gate, or in response to input of a signal for acquiring the image indicating the polarization state. Further, the λ/4 polarizing plate may be previously adjusted on an initial setting screen when activating the ophthalmologic apparatus, so that the λ/4 polarizing plate is not required to be adjusted for each image capturing.

Furthermore, if the λ/4 polarizing plate can be inserted and removed with respect to the optical path, it is desirable to perform adjustment in the following order: alignment adjustment using the anterior segment image or the luminescent spot in the cornea; focus adjustment using the SLO fundus image; coherence gate adjustment using the OCT tomographic image; and adjustment of the λ/4 polarizing plate after inserting the λ/4 polarizing plate in the optical path. Adjustment can thus be performed before acquiring the image indicating the polarization state, using the normal SLO fundus image and the OCT tomographic image that the user is intuitively used to. The coherence gate may also be adjusted using the tomographic image indicating the polarization state of the PS-OCT by inserting the λ/4 polarizing plate after performing focus adjustment. In such a case, the λ/4 polarizing plate may be automatically inserted in response to completion of adjustment of the coherence gate, or in response to input of the signal for acquiring the image indicating the polarization state.

Moreover, the focus may be finely adjusted using the OCT tomographic image after coarsely adjusting the focus using the SLO fundus image.

Further, all of such adjustments maybe automatically performed in the above-described order, or by the user adjusting the cursor to a slider corresponding to each type of adjustment displayed on the display unit and performing dragging. Furthermore, if the λ/4 polarizing plate is to be inserted or removed, an icon instructing inserting or removing the λ/4 polarizing plate with respect to the optical path may be displayed on the display unit.

Instep S102 and step S103 illustrated in FIG. 3, each of the light sources 101 and 141 emits the measuring beam. The line cameras 129 and 133 and the APD 152 and 153 then receive the return beam, and the image generation unit 193 generates each image as described above.

An intensity value of the tomographic image of an eye with a disease becomes lower than that of a healthy eye due to an effect of the disease, so that the retinal layer may be overlooked or falsely detected. To avoid such a problem, in step S104, the image analysis unit 194 detects each retinal layer using the information on the region that scrambles the polarization state of light, calculated by the image generation unit 193 in step S103.

More specifically, the RPE in the retinal layers scrambles the polarization state of light, as indicated by calculating the DOPU value using equation (4). The position of the RPE 210 can thus be detected. Further, the entire retinal layer 220 which does not scramble the polarization state of light can also be detected. As a result, the intensity value of the RPE for each tomographic image becomes recognizable by referring to the intensity value of the region corresponding to the RPE in the intensity image. All of the retinal layers, the position of the RPE, and the intensity value corresponding to the RPE thus become recognizable even in the tomographic image in which the intensity value becomes low due to the effect of the disease, so that an oversight or false detection can be prevented.

Boundaries of each of the retinal layers may be detected employing, as a threshold value for layer detection, the intensity value obtained from the position obtained by calculating the DOPU using equation (4). For example, the threshold value for acquiring the boundary of each layer in the healthy eye is preset. Further, an average intensity value of the RPE and all of the retinal layers is preset. The intensity value of the RPE obtained by equation (4), the intensity value of all of the retinal layers, and the preset average intensity value are then compared, and the preset threshold value for acquiring the boundary of each layer is adjusted according to a difference in the intensities in percentage terms. For example, if the intensity values of the intensity images corresponding to the RPE 210 and the retinal layers 220 illustrated in FIG. 2E are less than the preset average intensity value by 10%, the threshold value is reduced by 10%. The image analysis unit 194 then applies, to the tomographic image to be processed, a median filter as a type of a smoothing process, and a Sobel filter as a type of edge detection, and generates the respective images (hereinafter referred to as a median image and a Sobel image). The image analysis unit 194 generates a profile for each A-scan from the generated median image and Sobel image. The image analysis unit 194 generates the profile of the intensity value from the median image and the profile of a gradient from the Sobel image. The image analysis unit 194 then detects a peak in the profile generated from the Sobel image. The image analysis unit 194 refers to the profiles of the median images corresponding to regions before and after the peak and the regions between the peaks, compares them with the acquired threshold value, and thus extracts the boundary of each region in the retinal layers. The boundary of each region in the retinal layers includes an internal limiting membrane (ILM), a ganglion cell layer (GCL), an inner plexiform layer (IPL), an external limiting layer (ELM), and border between the photoreceptor inner and outer segments (IS/OS).

Figure 5A:
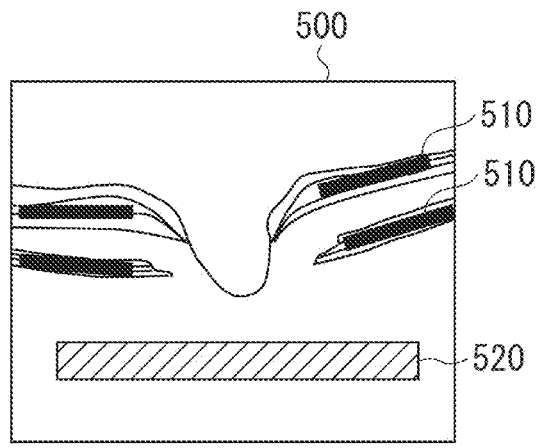
FIGS. 5A and 5B illustrate detection of the retinal layers according to the present exemplary embodiment.
Figure 5B:
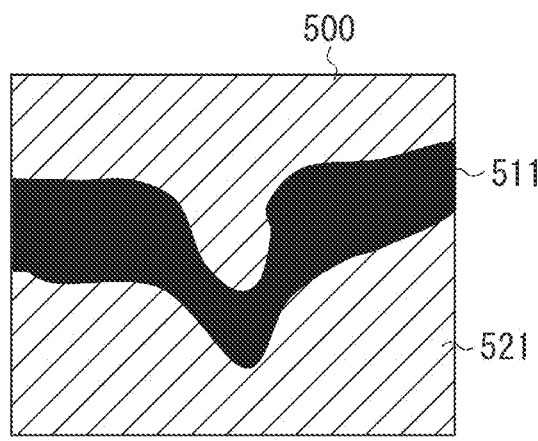

Further, the RPE 210 and the retinal layers 220 illustrated in FIG. 2E may be used as initial positions in a graph cut method, which is an example of the layer boundary detection method. The graph cut method assigns, to the image a label of either an object ("obj") or a background ("bkg"), minimizes an energy function related to the region and the boundary, and then detects the object. The graph cut method will be described below with reference to FIGS. 5A and 5B. FIG. 5A illustrates an example of an object label 510 and a background label 520. Referring to FIG. 5A, the object label 510 is assigned to the RPE 210 and a portion of the retinal layers 220 illustrated in FIG. 2E in an intensity image 500. Further, the background label 520 is assigned to a region of a portion below the RPE 210 by several tens of pixels. When the object and background labels are assigned to the pixels of a portion of the image in the graph cut method, the region is segmented into the object and the background using a minimum cut/minimum flow algorithm. FIG. 5B illustrates an example of region segmentation performed by the graph cut method. Referring to FIG. 5B, a black region 511 is the result of detecting the object ("obj"), and a shaded region 521 is the result of detecting the background ("bkg"). An inner layer boundary is thus detected within the acquired region of the object ("obj"). As a result, the object region can be previously detected, so that false detection and oversight can be prevented.

Figure 6A:
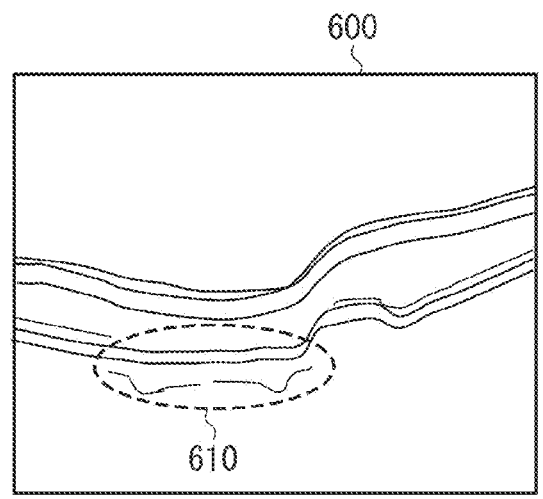
FIGS. 6A, 6B, and 6C illustrate detection of the retinal layers according to the present exemplary embodiment.
Figure 6B:
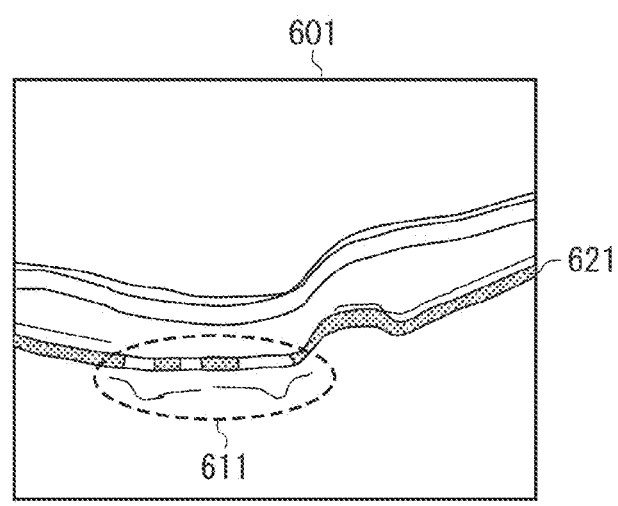
Figure 6C:
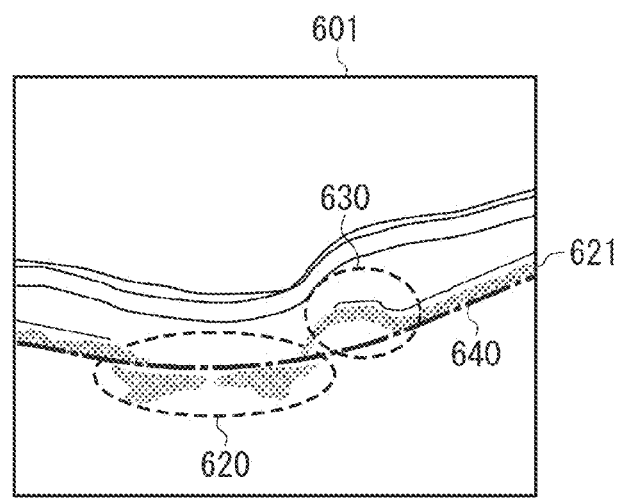

The image analysis unit 194, i.e., an example of the extraction unit, is capable of extracting (detecting), from the DOPU image, a region in which the polarization state is scrambled, such as the RPE layer. The region in which the polarization state is scrambled is a region in which the difference between the effects of the two polarized beams received by the subject's eye is comparatively large. If the RPE becomes irregular due to atrophy, the DOPU does not detect the irregular portion as the RPE, so that the atrophic portion of the RPE can be detected, which is advantageous. The atrophic portion of the RPE indicates a discontinuous portion or a missing portion of the RPE (i.e., an abnormal portion in the RPE). In such a case, if the shape of the retinal layer is to be analyzed, it is desirable to detect a Bruch membrane boundary line below the RPE. Normally, the RPE is in close contact with the Bruch membrane, so that the shape of the retinal layer can be acquired by detecting the RPE. If the shape of the RPE is irregular, the shape of the retinal layer can be acquired by detecting the Bruch membrane boundary. The Bruch membrane boundary line is detected by interpolating the region below the portion in which the RPE is not detected using surrounding RPE information. Such an example is illustrated in FIGS. 6A, 6B, and 6C. Referring to FIG. 6A, an area 610 surrounded by a broken-line oval in a tomographic intensity image 600 indicates an atrophic region in the RPE. Referring to FIG. 6B, an RPE 621 detected from the DOPU is superimposed and displayed on a tomographic intensity image 601. A region 611 surrounded by a broken-line oval is a region that is not detected from the DOPU and in which the Bruch membrane boundary line is to be detected. In other words, if the tomographic intensity image is to be used for analyzing the shape of the retinal layer, the Bruch membrane boundary is detected in the region illustrated in FIG. 6B. The Bruch membrane boundary is detected by searching for an edge in a direction adjacent to ends of the region in which the RPE is continuous. Further, the Bruch membrane is detected using points in the region in which the RPE is smoothly changing, and performing function approximation employing robust estimation such as M estimation. Whether the RPE is smoothly changing can be determined by calculating a curvature at each point in the RPE and identifying the region which is smoothly changing. More specifically, whether the retinal layer is smoothly changing can be determined by obtaining the change in the curvature value of each point in the layer boundary as will be described below. Further, if the region in which the polarization state is scrambled is superimposed and displayed on the tomographic intensity image, the user can easily recognize the positional relation between the retinal layers and the abnormal portion in the RPE. The subject's eye can thus be effectively diagnosed.

Furthermore, the image analysis unit 194 can extract the RNFL from the retardation image. As a result, the image analysis unit 194 can extract, from the tomographic image indicating the polarization state, the layer corresponding to the type of the tomographic image. Moreover, if the image analysis unit 194 extracts the RPE from the DOPU image and the RNFL from the retardation image, the display control unit 191 can display, on the display unit 192, the extracted layers superimposed on the tomographic intensity image. In such a case, the display control unit 191 can display the RPE and the RNFL in different display forms, such as superimpose on the tomographic image using different colors. Further, it is desirable to selectively perform a three-dimensional display of the layers, or calculate distances of the layers. As a result, the user can effectively diagnose the subject's eye based on such information.

The process for outputting the generated images and the analysis results performed in step S105 will be described below.

When the image generation unit 193 and the image analysis unit 194 in the signal processing unit 190 complete generation and analysis of each image, the control unit 191 generates output information based on the results, and outputs to and displays on the display unit 192 the generated information.

Figure 7:
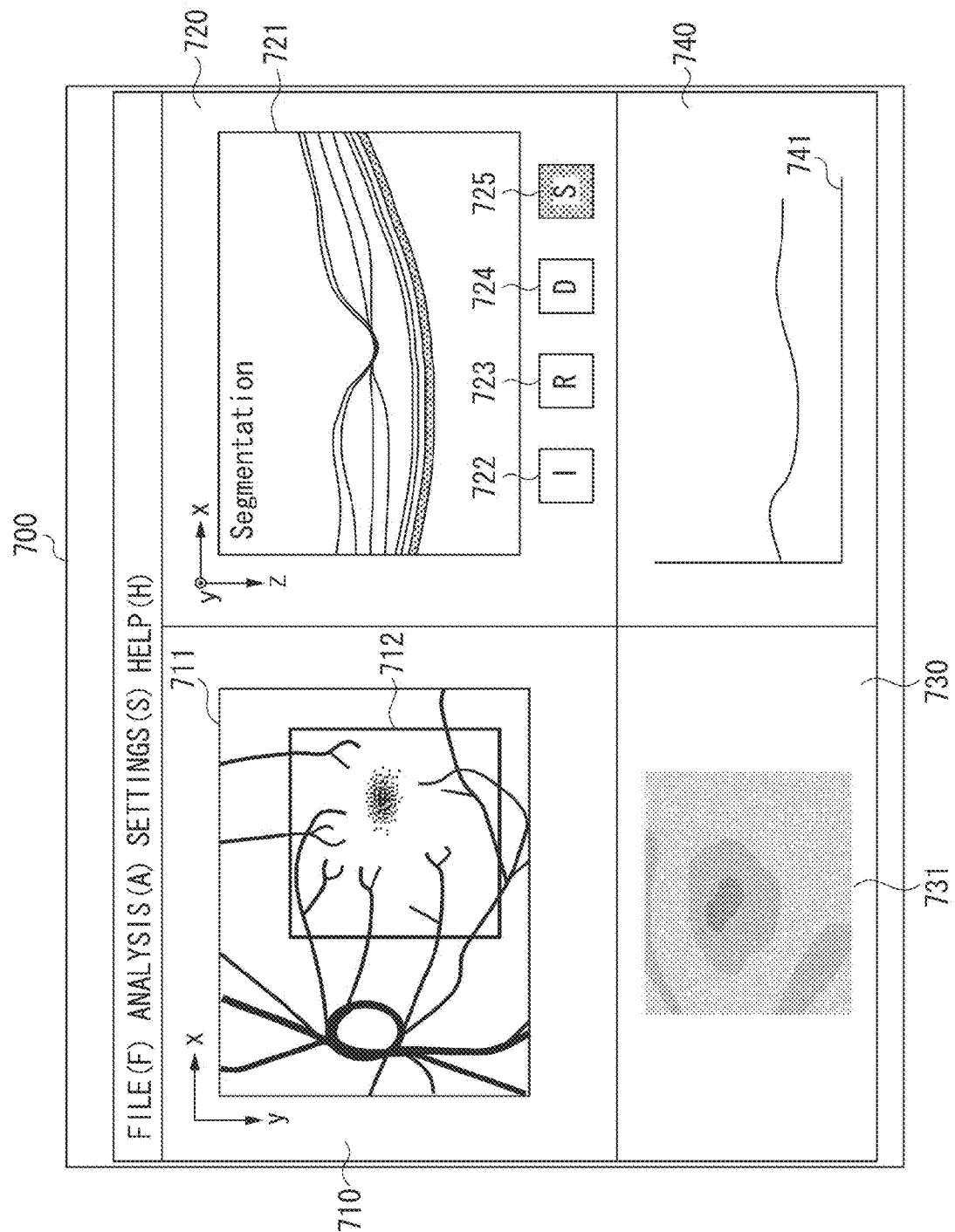
FIG. 7 illustrates a display example of the display screen on the display unit in the image processing apparatus according to the present exemplary embodiment.

FIG. 7 illustrates a display example on the display unit 192 according to the present exemplary embodiment.

Referring to FIG. 7, a window 700 displayed on the display unit 192 includes display areas 710, 720, 730, and 740.

The display area 710, i.e., an example of a first display area, displays a fundus image 711, and a rectangular frame 712 indicating the position of the tomographic image is superimposed on the fundus image 711. The fundus intensity image is displayed as the fundus image 711. However, the fundus image generated based on a polarization signal maybe displayed.

The display area 720, i.e., an example of a second display area, displays a tomographic image 721. Further, displays buttons 722, 723, 724, and 725, i.e., examples of a selection unit for selecting the type of the tomographic image to be displayed, are displayed on the display area 720. The user may select the type of the tomographic image from a menu instead of using the buttons 722, 723, 724, and 725. In the example illustrated in FIG. 7, the user has selected the button 725, so that a segmentation result is displayed to be superimposed on the tomographic intensity image, and the RPE is highlighted. The other buttons 722, 723, and 724, and the displaying content thereof will be described below. If the operator presses the button 722, the tomographic intensity image is displayed on the display area 720. If the operator presses the button 723, the retardation image is displayed on the display area 720. If the operator presses the button 724, the DOPU image is displayed on the display area 720.

It is desirable to display the segmentation image 721, the tomographic intensity image, and the retardation image and the DOPU image to be described below, by superimposing a display form indicating the type of the image, such as "segmentation", "intensity", "retardation", and "DOPU" in characters. As a result, the user is prevented from misrecognizing the image. The image type may be displayed above or besides the image instead of superimposing on the image, as long as the display form corresponds to the image.

Further, thickness information 731 of the selected layer may be displayed on the display area 730, i.e., an example of the third display area. The thickness information 731 expresses the thickness of the selected layer by a difference in the color. An integration image may be displayed in place of the thickness of the selected layer illustrated in the thickness information 731. The integration image may be based on a specific layer or on the entire PS-OCT. Further, according to the present exemplary embodiment, the image to be displayed is changed according to the instruction of the operator. However, the information on the disease to be diagnosed, such as the name of the disease, may be selected from the menu, and the image on which a priority order has been preset with respect to the disease may be displayed on each display area. Furthermore, the display area 740, i.e., an example of the fourth display area, may display a graph 741 indicating the layer thickness. The user can then confirm a structural change in the PS-OCT associated with the structure of the retinal layers, so that the subject's eye can be effectively diagnosed.

Moreover, the display control unit 191 may display, on one of the display areas in the display unit 192, the retardation map or the birefringence map instead of the above-described images. Further, the display control unit 191 may superimpose on the fundus intensity image 711 and display the retardation map and the birefringence map. In such a case, it is desirable to superimpose and display the retardation map and the birefringence map on the area indicated by the frame 712.

As described above, according to the present exemplary embodiment, the retinal layers can be accurately detected from the tomographic image acquired from the polarization-sensitive OCT.

According to the present exemplary embodiment, the positions of the display areas in which the above-described images are displayed are not limited thereto. For example, the fundus image may be displayed in a left display area in the display screen. Further, the number of images to be displayed is not limited thereto. For example, the fundus image and the tomographic image (i.e., two images) may be displayed side by side on the display screen when performing adjustment. The display method may then be changed after performing imaging, and a plurality of tomographic images indicating different polarizing states may be displayed side by side on the display screen along with the fundus image. Furthermore, the order and the positions in which the buttons 722, 723, 724, and 725 are arranged are not limited thereto.

Figure 8:
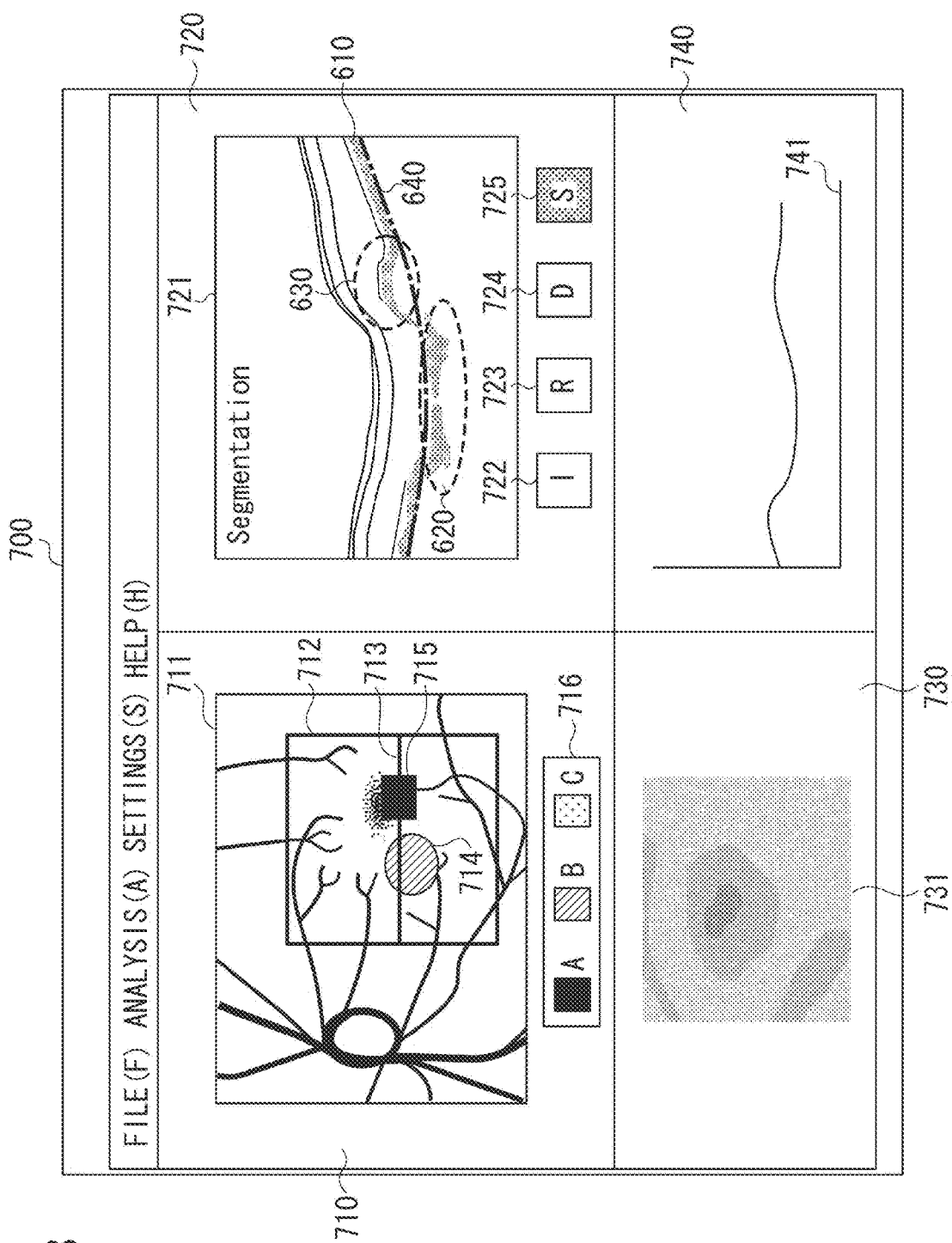
FIG. 8 illustrates a display example of a display screen on a display unit in an image processing apparatus according to another exemplary embodiment.

A case where the regions in which the polarization state is scrambled exist above and below a reference line according to another aspect of the present invention will be described below with reference to FIGS. 6C and 8. FIG. 8 illustrates a display example of the display screen on the display unit in the image processing apparatus according to the present exemplary embodiment.

The image analysis unit 194 detects each retinal layer and identifies a lesion portion using the information on the region in which the polarization state is scrambled. FIG. 6C illustrates, using a dashed-dotted line, a reference line 640 detected based on the information on the RPE acquired by the image analysis unit 194 performing boundary detection of the retinal layer. Further, regions 620 and 630 circled by dotted lines are examples of indices indicating different positions in a depth direction of the subject's eye in the region in which the polarization state is scrambled. The regions 620 and 630 indicate characteristic regions existing above and below the reference line 640. It is desirable to display each of the regions 620 and 630 differently, such as use different colors, so that the different positions are identifiable in the region in which the polarization state is scrambled.

A method for estimating the reference line 640 will be described below. An input three-dimensional topographic image is considered as a set of two-dimensional topographic images (i.e., B-scan images), and the reference line is estimated with respect to each of the two-dimensional topographic images. Such a method estimates the reference line by applying an N-th order curve to a coordinate point group indicating the layer boundary detected in the focused two-dimensional topographic image. According to the present exemplary embodiment, the reference line 640 is obtained by applying a quadratic curve to the RPE layer detected by the image analysis unit 194. The quadratic curve is estimated using robust estimation such as M estimation and LMedS.

If the region in which the polarization state is scrambled includes an abnormal range (i.e., the lesion portion), it is desirable to estimate the reference line by selecting the coordinate point group from the region excluding than the abnormal range. The lesion portion is identified using the curvature value of each point in the region in which the polarization state is scrambled. More specifically, if the curvature value is outside a predetermined range, the lesion portion is assumed to have a predetermined shape. The curvature value is a value defined, when approximating by a circle a predetermined range from each point in the region in which the polarization state is scrambled, as an inverse of the radius of the circle, i.e., the curvature of the circle. If the radius of the circle is comparatively large, the curvature value becomes close to 0. The lesion portion is a portion where the change in the shape is great in the region in which the polarization state is scrambled. The radius of the circle thus becomes comparatively small, and an absolute value of the curvature value becomes comparatively large at the lesion portion.

If the curvature value of each point in the layer boundary changes smoothly, the retinal layers is defined as normal. In such a case, the portion in which the curvature does not change smoothly is determined to be the abnormal range by calculating a local curvature value of the detected layer boundary, and evaluating the shape of the layer boundary. For example, the region 630 illustrated in FIG. 6C is the range in which the curvature value is not changing smoothly. Further, the abnormal range by detecting a leukoma, a hemorrhage, or a drusen from the fundus image, and the retinal layer in a z-direction of the tomographic image corresponding to an (x, y) region in which the lesion portion exists in a wide-area image is determined as abnormal. Further, the abnormal range may be determined based on a ratio in the three-dimensional tomographic image of an area in which the regions that scramble the polarization state of light, acquired by performing the DOPU calculation, continuously occur. For example, the region 620 illustrated in FIG. 6C is an isolated region when viewed in the three-dimensional tomographic image. Furthermore, the region in which a thickness of the region that scrambles the polarization state of light is outside the normal range may be determined as the abnormal range. The normal range can be determined by comparison with statistical data collected from a plurality of data of the normal eye.

The reference line 640 is thus estimated by excluding the lesion portion as described above, so that the reference line can be set at the position which is originally the position of the RPE.

FIG. 8 illustrates the display example on the display unit 192 according to the present exemplary embodiment. Referring to FIG. 8, a window 700 displayed on the display unit 192 includes the display areas 710, 720, 730, and 740.

The display area 710, i.e., an example of the first display area, displays the fundus image 711, and the rectangular frame 712 indicating the position of the tomographic image and a line 713 indicating the position of the tomographic image 721 are superimposed on the fundus image 711. The fundus intensity image is displayed as the fundus image 711. However, the fundus image based on a polarization signal may be displayed. Indices 714 and 715 are displayed on the fundus image so that the difference in the types of lesion is distinguishable. According to the present exemplary embodiment, the circular-shaped index 714 indicates the abnormal range 620, and the square-shape index 715 indicates the abnormal range 630. The indices are thus displayed according to the difference in physical features of the retinal layer due to the difference in the type of lesion, so that the difference between the types becomes determinable on the fundus image. The difference between the types of lesion becomes identifiable by the difference in the physical features, such as whether the region in which the polarization state is scrambled exists above the reference line 640 (i.e., a shallow position with respect to the depth direction of the retina) or below the reference line 640. It is desirable to display the portion of the region that scrambles the polarization state of light, which exists below the reference line 640 (i.e., the shallow position with respect to the depth direction of the retina), by a different color from the other portions, such as the portion existing above the reference line 640. As a result, the user can easily distinguish the type of lesion.

The portion in the layer structure of the RPE which is continuous, and the portion which is missing can also be distinguishably displayed. The indices 714 and 715 can be displayed by changing the color, changing the shape, e.g., to a circle, a square, or a triangle, according to the type of lesion, or changing both. The operator is capable of switching, using the instruction device (not illustrated) such as the mouse, between displaying by superimposing on the image and not displaying the indices according to the types of lesion.

Lesion type information 716 for indicating what the indices (715 and 716) that differ according to the type of lesion represent, is displayed in the vicinity of the fundus image. According to the present exemplary embodiment, the types of the lesion are indicated by indices of different colors, so that the lesion type information displays the colors and the corresponding types of lesions. For example, it is desirable to display such that red indicates an atrophic form of macular degeneration, and purple indicates exudative macular degeneration. Further, a degree of the lesion may be indicated by color density. For example, if the index is light-colored, the lesion is of a slight degree, and if the index is dark-colored, the lesion is of a severe degree. It is not necessary for the lesion type information 716 to be as described above, and may be displayed so that the shape of the index and the type of lesion are distinguishable.

The display area 720, i.e., an example of the second display area, displays a tomographic image 721. Further, the buttons 722, 723, 724, and 725, i.e., examples of the selection unit for selecting the type of the tomographic image to be displayed, are displayed on the display area 720. The user may select the type of the tomographic image from a menu instead of using the buttons 722, 723, 724, and 725. In the example illustrated in FIG. 7, the user has selected the button 725, so that the segmentation result is displayed by being superimposed on the tomographic intensity image, and the RPE is highlighted. The other buttons 722, 723, and 724, and the displaying content thereof will be described below. If the operator presses the button 722, the tomographic intensity image is displayed on the display area 720. If the operator presses the button 723, the retardation image is displayed on the display area 720. If the operator presses the button 724, the DOPU image is displayed on the display area 720.

It is desirable to display the segmentation image 721, the tomographic intensity image, and the retardation image and the DOPU image to be described below, by superimposing a display form indicating the type of the image, such as "segmentation", "intensity", "retardation", and "DOPU" in characters. As a result, the user is prevented from misrecognizing the image. The type of the image may be displayed above or besides the image instead of superimposing on the image, as long as the display form corresponds to the image.

Further, the thickness information 731 of the selected layer may be displayed on the display area 730, i.e., an example of the third display area. The thickness information 731 expresses the thickness of the selected layer by a difference in the color. The integration image may be displayed in place of the thickness of the selected layer illustrated in the thickness information 731. The integration image may be based on a specific layer or on the entire PS-OCT. Further, according to the present exemplary embodiment, the image to be displayed is changed according to the instruction of the operator. However, the information on the disease to be diagnosed, such as the name of the disease, may be selected from the menu, and the image on which a priority order has been preset with respect to the disease may be displayed on each display area. Furthermore, the display area 740, i.e., an example of the fourth display area, may display the graph 741 indicating the layer thickness.

Moreover, the display control unit 191 may display, on one of the display areas in the display unit 192, the retardation map or the birefringence map instead of the above-described images. Further, the display control unit 191 may superimpose on the fundus intensity image 711 and display the retardation map and the birefringence map. In such a case, it is desirable to superimpose and display the retardation map and the birefringence map on the area indicated by the frame 712.

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., a non-transitory computer-readable medium).

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Applications No. 2012-010279 filed Jan. 20, 2012 and No. 2012-186592 filed Aug. 27, 2012, which are hereby incorporated by reference herein in their entirety.

What is claimed is:
1. An image processing apparatus comprising:
an acquisition unit configured to acquire a polarization-sensitive tomographic image of a fundus of an eye, the polarization-sensitive tomographic image including a degree of polarization uniformity (DOPU) image and a retardation image;
an extraction unit configured to extract a region including a retinal pigment epithelium layer of the fundus using the DOPU image and a region including a retinal nerve fiber layer of the fundus using the retardation image;

a selection unit configured to select at least one of the extracted region including the retinal pigment epithelium layer and the extracted region including the retinal nerve fiber layer; and a display control unit configured to cause a display unit to display the selected at least one of the extracted region including the retinal pigment epithelium layer and the extracted region including the retinal nerve fiber layer.

2. The image processing apparatus according to claim 1, wherein the extraction unit extracts, from the polarization-sensitive tomographic image, a layer corresponding to a type of the polarization-sensitive tomographic image.

3. The image processing apparatus according to claim 1, further comprising a display control unit configured to causes a display unit to display the extracted regions, to be superimposed on a tomographic intensity image of the fundus.

4. The image processing apparatus according to claim 1, further comprising a display control unit configured to causes a display unit to display the extracted region including the retinal pigment epithelium layer and the extracted region including the retinal nerve fiber layer in different display forms, to be superimposed on a tomographic intensity image of the fundus.

5. The image processing apparatus according to claim 3, wherein the display control unit causes the display unit to display indices indicating different positions in a depth direction of the eye in the extracted regions.

6. The image processing apparatus according to claim 3, wherein the display control unit causes the display unit to display, display forms that are different for each of different positions in a depth direction of the subject in the extracted regions.

7. The image processing apparatus according to claim 3, further comprising an estimation unit configured to estimate a reference line of the extracted regions, wherein the displays causes display unit to display, display forms that are different for each of different positions in a depth direction of the subject with respect to the reference line.

8. The image processing apparatus according to claim 1, wherein the display control unit causes the display unit to perform three-dimensional display of the selected at least one of the extracted region including the retinal pigment epithelium layer and the extracted region including the retinal nerve fiber layer.

9. The image processing apparatus according to claim 1, further comprising a calculation unit configured to calculate a distance between the extracted regions.

10. The image processing apparatus according to claim 1, wherein the acquisition unit acquires the polarization-sensitive tomographic image based on beams of different polarizations obtained by splitting a combined beam into which a return beam from the subject irradiated with a measuring beam and a reference beam corresponding to the measuring beam have been combined.

11. The image processing apparatus according to claim 1, further comprising a determination unit configured to determine a threshold using the DOPU image, wherein the extraction unit extracts the retinal pigment epithelium layer from a tomographic intensity image of the fundus using the determined threshold.

12. An image processing method comprising:

acquiring a polarization-sensitive tomographic image of a fundus of an eye, the polarization-sensitive tomographic image including a degree of polarization uniformity (DOPU) image and a retardation image;

extracting a region including a retinal pigment epithelium layer of the fundus using the DOPU image and a region including a retinal nerve fiber layer of the fundus using the retardation image;

selecting at least one of the extracted region including the retinal pigment epithelium layer and the extracted region including the retinal nerve fiber layer; and causing a display unit to display the selected at least one of the extracted region including the retinal pigment epithelium layer and the extracted region including the retinal nerve fiber layer.

13. A non-transitory computer-readable storage medium storing a program that causes a computer to execute the image processing method according to claim 12.

14. The image processing method according to claim 12, further comprising causing a display unit to display the extracted region including the retinal pigment epithelium layer and the extracted region including the retinal nerve fiber layer in different display forms, to be superimposed on a tomographic intensity image of the fundus.

15. The image processing method according to claim 12, wherein the display unit is caused to perform three-dimensional display of the selected at least one of the extracted region including the retinal pigment epithelium layer and the extracted region including the retinal nerve fiber layer.

16. The image processing method according to claim 12, further comprising calculating a distance between the extracted regions.

17. The image processing method according to claim 12, wherein the polarization-sensitive tomographic image is acquired based on beams of different polarizations obtained by splitting a combined beam into which a return beam from the subject irradiated with a measuring beam and a reference beam corresponding to the measuring beam have been combined.

18. The image processing method according to claim 12, further comprising determining a threshold using the DOPU image, wherein the retinal pigment epithelium layer is extracted from a tomographic intensity image of the fundus using the determined threshold.

19. An image processing apparatus comprising:

an acquisition unit configured to acquire a polarization-sensitive tomographic image of an object; and an extraction unit configured to extract a region in which a polarization state is scrambled from the polarization-sensitive tomographic image and to extract a predetermined layer from a tomographic intensity image of the object using a part of the extracted region.

20. The image processing apparatus according to claim 19, wherein the object includes an eye, wherein the polarization-sensitive tomographic image includes a degree of polarization uniformity (DOPU) image of a fundus of the eye, and wherein the extraction unit extracts, from the DOPU image, a region including a retinal pigment epithelium layer of the fundus.

21. The image processing apparatus according to claim 19, wherein the object includes an eye, wherein the polarization-sensitive tomographic image includes a retardation image of a fundus of the eye, and wherein the extraction unit extracts, from the retardation image, a region including a retinal nerve fiber layer of the fundus.

22. The image processing apparatus according to claim 19, wherein the extraction unit uses information on the region in which the polarization state is scrambled as a threshold value for extracting a boundary of a retinal layer.

23. The image processing apparatus according to claim 19, wherein the extraction unit uses information on the region in which the polarization state is scrambled as an initial position for extracting a boundary of a retinal layer.

24. The image processing apparatus according to claim 19, wherein the extraction unit detects a boundary of a retinal layer by interpolating the boundary of the retinal layer according to whether the extracted regions exists.

25. The image processing apparatus according to claim 19, wherein the object includes an eye,
wherein the polarization-sensitive tomographic image includes a degree of polarization uniformity (DOPU) image of a fundus of the eye and a retardation image of the fundus, and
wherein the extraction unit extracts the region in which the polarization state is scrambled from the DOPU image, extracts, as the predetermined layer, a retinal pigment epithelium layer of the fundus from the tomographic intensity image using the part of the extracted region, and extracts a retinal nerve fiber layer of the fundus from the retardation image.

26. The image processing apparatus according to claim 25, further comprising a display control unit configured to causes a display unit to display the extracted retinal pigment epithelium layer and the extracted retinal nerve fiber layer in different display forms, to be superimposed on a tomographic intensity image of the fundus.

27. The image processing apparatus according to claim 25, further comprising:
a selection unit configured to select at least one of the extracted retinal pigment epithelium layer and the extracted retinal nerve fiber layer; and
a display control unit configured to cause a display unit to perform three-dimensional display of the selected at least one of the extracted retinal pigment epithelium layer and the extracted retinal nerve fiber layer.

28. The image processing apparatus according to claim 25, further comprising a calculation unit configured to calculate a distance between the extracted layers.

29. The image processing apparatus according to claim 19, wherein the acquisition unit acquires the polarization-sensitive tomographic image based on beams of different polarizations obtained by splitting a combined beam into which a return beam from the subject irradiated with a measuring beam and a reference beam corresponding to the measuring beam have been combined.

30. The image processing apparatus according to claim 19, wherein the object includes an eye,
wherein the polarization-sensitive tomographic image includes a degree of polarization uniformity (DOPU) image of a fundus of the eye, and
wherein the extraction unit extracts the region in which the polarization state is scrambled from the DOPU image and extracts, as the predetermined layer, a retinal pigment epithelium layer of the fundus from the tomographic intensity image using the part of the extracted region.

31. The image processing apparatus according to claim 19, further comprising a determination unit configured to determine, using the part of the extracted region, a threshold of extracting the predetermined layer from the tomographic intensity image,
wherein the extraction unit extracts the predetermined layer from the tomographic intensity image using the determined threshold.

32. An image processing method comprising:
acquiring a polarization-sensitive tomographic image of an object; and
extracting a region in which a polarization state is scrambled from the polarization-sensitive tomographic image and extracting a predetermined layer from a tomographic intensity image of the object using a part of the extracted region.

33. A non-transitory computer-readable storage medium storing a program that causes a computer to execute the image processing method according to claim 32.

34. The image processing method according to claim 32, wherein the object includes an eye,
wherein the polarization-sensitive tomographic image includes a degree of polarization uniformity (DOPU) image of a fundus of the eye and a retardation image of the fundus, and
wherein the region in which the polarization state is scrambled is extracted from the DOPU image, a retinal pigment epithelium layer of the fundus is extracted, as the predetermined layer, from the tomographic intensity image using the part of the extracted region, and a retinal nerve fiber layer of the fundus is extracted from the retardation image.

35. The image processing method according to claim 34, further comprising causing a display unit to display the extracted retinal pigment epithelium layer and the extracted retinal nerve fiber layer in different display forms, to be superimposed on a tomographic intensity image of the fundus.

36. The image processing method according to claim 34, further comprising:
selecting at least one of the extracted retinal pigment epithelium layer and the extracted retinal nerve fiber layer; and
causing a display unit to perform three-dimensional display of the selected at least one of the extracted retinal pigment epithelium layer and the extracted retinal nerve fiber layer.

37. The image processing method according to claim 34, further comprising calculating a distance between the extracted layers.

38. The image processing method according to claim 32, wherein the polarization-sensitive tomographic image is acquired based on beams of different polarizations obtained by splitting a combined beam into which a return beam from the subject irradiated with a measuring beam and a reference beam corresponding to the measuring beam have been combined.

39. The image processing method according to claim 32, wherein the object includes an eye,
wherein the polarization-sensitive tomographic image includes a degree of polarization uniformity (DOPU) image of a fundus of the eye,
wherein the region in which the polarization state is scrambled is extracted from the DOPU image, and
wherein a retinal pigment epithelium layer of the fundus is extracted, as the predetermined layer, from the tomographic intensity image using the part of the extracted region.

40. The image processing method according to claim 32, further comprising determining, using the part of the extracted region, a threshold of extracting the predetermined layer from the tomographic intensity image, wherein the predetermined layer is extracted from the tomographic intensity image using the determined threshold.

41. An image processing apparatus comprising:
an acquisition unit configured to acquire a polarization-sensitive tomographic image of a fundus of an eye, the polarization-sensitive tomographic image including a degree of polarization uniformity (DOPU) image and a retardation image;
an extraction unit configured to extract a region including a retinal pigment epithelium layer of the fundus from the DOPU image and a region including a retinal nerve fiber layer of the fundus from the retardation image; and
a display control unit configured to cause a display unit to display the extracted region including the retinal pigment epithelium layer and the extracted region including the retinal nerve fiber layer in different display forms, to be superimposed on a tomographic intensity image of the fundus.

42. An image processing method comprising:
acquiring a polarization-sensitive tomographic image of a fundus of an eye, the polarization-sensitive tomographic image including a degree of polarization uniformity (DOPU) image and a retardation image;
extracting a region including a retinal pigment epithelium layer of the fundus from the DOPU image and a region including a retinal nerve fiber layer of the fundus from the retardation image; and
causing a display unit to display the extracted region including the retinal pigment epithelium layer and the extracted region including the retinal nerve fiber layer in different display forms, to be superimposed on a tomographic intensity image of the fundus.

43. A non-transitory computer-readable storage medium storing a program that causes a computer to execute the image processing method according to claim 42.

* * * * *